(12) United States Patent
Komoto (10) Patent No.: US 10,605,760 B2
(45) Date of Patent: Mar. 31, 2020

(54) THIN FILM-LAMINATED FILM

(71) Applicant: TOYOBO CO., LTD., Osaka (JP)

(72) Inventor: Munenori Komoto, Otsu (JP)

(73) Assignee: TOYOBO CO., LTD., Osaka (JP)

(*) Notice: Subject to any disclaimer, the term of this patent is extended or adjusted under 35 U.S.C. 154(b) by 110 days.

(21) Appl. No.: 15/327,083

(22) PCT Filed: Jul. 16, 2015

(86) PCT No.: PCT/JP2015/070381
§ 371 (c)(1),
(2) Date: Jan. 18, 2017

(87) PCT Pub. No.: WO2016/013478
PCT Pub. Date: Jan. 28, 2016

(65) Prior Publication Data
US 2017/0153200 A1 Jun. 1, 2017

(30) Foreign Application Priority Data

Jul. 22, 2014 (JP) ................................. 2014-148714
Oct. 9, 2014 (JP) ................................. 2014-207772

(51) Int. Cl.
*G01N 27/327* (2006.01)
*B32B 15/08* (2006.01)
(Continued)

(52) U.S. Cl.
CPC ......... *G01N 27/3275* (2013.01); *B32B 3/266* (2013.01); *B32B 15/08* (2013.01);
(Continued)

(58) Field of Classification Search
CPC ............ G01N 27/3275; G01N 27/308; G01N 27/327; C23C 14/205; C23C 14/14; C23C 14/35; C23C 14/0605; B32B 15/08
See application file for complete search history.

(56) References Cited

U.S. PATENT DOCUMENTS 5,677,003 A * 10/1997 Lee ...................... C23C 14/022
427/122
6,410,125 B1 * 6/2002 Brenner .................... C23C 8/24
427/457
(Continued)

FOREIGN PATENT DOCUMENTS

CN 103201619 7/2013
JP S62-059499 A * 3/1987
(Continued)

OTHER PUBLICATIONS

Machine translation to English of JP 2013-185991, A (Year: 2013).*
(Continued)

*Primary Examiner* — J. Christopher Ball
(74) *Attorney, Agent, or Firm* — Wenderoth, Lind & Ponack, L.L.P.

(57) ABSTRACT

The present invention provides the following thin film-laminated film that has high chemical stability even at low costs and that can preferably be used as an electrode film of a strip for a blood sugar level sensor. The thin film-laminated film including a film substrate, and a titanium thin film and a carbon thin film laminated in this order on at least one surface of the film substrate. Preferably, the above-described thin film-laminated film, in which the titanium thin film has a film thickness of from 10 to 400 nm, and the carbon thin film has a film thickness of from 0.2 to 50 nm. In addition, a strip for a blood sugar level sensor, including the above-described thin film-laminated film. Further, a blood sugar level sensor device including the above-described strip for a blood sugar level sensor.

5 Claims, 3 Drawing Sheets

(51) Int. Cl.

| | |
|---|---|
| *C23C 14/20* | (2006.01) |
| *B32B 27/28* | (2006.01) |
| *B32B 27/36* | (2006.01) |
| *B32B 3/26* | (2006.01) |
| *B32B 27/30* | (2006.01) |
| *B32B 27/32* | (2006.01) |
| *B32B 27/08* | (2006.01) |
| *B32B 23/20* | (2006.01) |
| *B32B 27/34* | (2006.01) |
| *B32B 27/20* | (2006.01) |
| *B32B 23/08* | (2006.01) |
| *B32B 27/16* | (2006.01) |
| *C23C 14/06* | (2006.01) |
| *C23C 14/14* | (2006.01) |
| *C23C 14/35* | (2006.01) |
| *G01N 27/30* | (2006.01) |

(52) U.S. Cl.
CPC ............ *B32B 23/08* (2013.01); *B32B 23/20* (2013.01); *B32B 27/08* (2013.01); *B32B 27/16* (2013.01); *B32B 27/20* (2013.01); *B32B 27/281* (2013.01); *B32B 27/286* (2013.01); *B32B 27/288* (2013.01); *B32B 27/302* (2013.01); *B32B 27/304* (2013.01); *B32B 27/306* (2013.01); *B32B 27/32* (2013.01); *B32B 27/34* (2013.01); *B32B 27/36* (2013.01); *B32B 27/365* (2013.01); *C23C 14/0605* (2013.01); *C23C 14/14* (2013.01); *C23C 14/205* (2013.01); *C23C 14/35* (2013.01); *G01N 27/308* (2013.01); *B32B 2250/02* (2013.01); *B32B 2250/03* (2013.01); *B32B 2250/40* (2013.01); *B32B 2255/10* (2013.01); *B32B 2255/20* (2013.01); *B32B 2255/205* (2013.01); *B32B 2255/28* (2013.01); *B32B 2307/202* (2013.01); *B32B 2307/40* (2013.01); *B32B 2307/416* (2013.01); *B32B 2457/00* (2013.01); *B32B 2535/00* (2013.01); *G01N 27/327* (2013.01)

(56) References Cited

U.S. PATENT DOCUMENTS

| | | |
|---|---|---|
| 2001/0028926 A1* | 10/2001 | Strondl .................. C23C 14/025 427/561 |
| 2003/0224216 A1 | 12/2003 | Hiratsuka et al. |
| 2006/0102229 A1 | 5/2006 | Miyoshi et al. |
| 2009/0324892 A1 | 12/2009 | Hasegawa et al. |
| 2012/0118735 A1 | 5/2012 | Kim et al. |
| 2013/0228461 A1 | 9/2013 | Kim |

FOREIGN PATENT DOCUMENTS

| | | |
|---|---|---|
| JP | 2003082458 A * | 3/2003 |
| JP | 2004-55114 | 2/2004 |
| JP | 2006-147261 | 6/2006 |
| JP | 2010-176876 | 8/2010 |
| JP | 2011-50300 | 3/2011 |
| JP | 2012-524903 | 10/2012 |
| JP | 2013-164350 | 8/2013 |
| JP | 2013-185991 | 9/2013 |
| WO | 2007/108394 | 9/2007 |

OTHER PUBLICATIONS

Translation of Abstract for JP S62-059499, A (Year: 1987).*
R. Schlesinger, et al. "Development of Thin Film Electrodes Based on Sputtered Amorphous Carbon", Journal of the Electrochemical Society, 144(1): p. 6-15, Jan. 1997.*
T. Laurila, et al., "Diamond-like carbon (DLC) thin film bioelectrodes: Effect of thermal post-treatments and the use of Ti adhesion layer" Material Science and Engineering C, vol. 34, pp. 446-454, Jan. 1, 2014.*
T. Laurila, et al. "Diamond-like carbon (DLC) thin film bioelectrodes: Effect of thermal post-treatments and the use of Ti adhesion layer", Material Science and Engineering C, 34, p. 446-454. Jan. 2014.*
International Search Report dated Sep. 8, 2015 in International Application No. PCT/JP2015/070381.
Office Action dated Jan. 7, 2019 in corresponding Taiwanese Patent Application No. 104123501, with English Translation.

* cited by examiner

THIN FILM-LAMINATED FILM

TECHNICAL FIELD

The present invention relates to a thin film-laminated film preferably used as an electrode film, and specifically relates to a thin film-laminated film preferably used as an electrode film for a blood sugar level sensor due to its superior electrochemical property and chemical resistance.

BACKGROUND ART

A blood sugar level sensor is used for measuring a blood sugar level once in several days to several times in a day, and controlling the measured values in a diabetic patient or a diabetic suspect. As a measurement strip for a blood sugar level sensor, a strip including a base substrate such as a plastic film having a patterned gold thin film is used (see PTD 1). The reason is that gold has low resistance value and high chemical stability that are directly linked to reliability as a sensor.

On the other hand, although there have been a lot of diabetic patients around Europe and America, recently the number of the patients are on upward trend in the whole world such as in Japan, China, and India. Thus, a low cost strip for a blood sugar level sensor has become required. Accordingly, a low cost electrode material without using gold has become required.

As a low cost strip for a blood sugar level sensor, a strip is disclosed which is obtained by depositing a nickel layer with the use of sputtering as one of vacuum deposition methods, and further depositing a carbon layer on the nickel layer to produce an electrode film, and then pattern processing the resultant electrode film (see PTD 2). An electrode material is required to have chemical stability against an electron mediator (a compound mediating electron transfer), such as potassium ferricyanide, having an oxidative effect, a buffer showing acidity or alkalinity, and the like contained in a reagent layer of a strip. The reason for providing a carbon layer on nickel is solely to compensate for low chemical stability of nickel with a carbon layer. The nickel layer is protected to some extent from an acid or an alkali, since the nickel layer is covered over with the carbon layer. However, nickel comes in contact with the reagent layer at a lateral face of the patterned electrode, and this can lead to elution of nickel. Accordingly, an abnormal sensor signal can be observed, or the electrode can be exfoliated.

Further, as another low cost strip for a blood sugar level sensor, a strip is disclosed in which a carbon layer is formed on a substrate, and a metal, such as silver or aluminum, is laminated by vacuum deposition at a region excluding a portion where the carbon layer comes in contact with a chemical reaction portion (see PTD 3). The above technique has been employed because when a metal, such as silver, layer is laminated in advance, and then a carbon layer is laminated on the metal layer, the metal layer is oxidized to increase contact resistance with the carbon layer. Besides, in the same cited literature, the carbon layer is formed by printing ink containing a carbon pigment and an organic binder; however, as a result of a combined use of the printing and a subsequent deposition method of a metal layer via vacuum vapor-deposition method, industrial productivity is significantly decreased, and the carbon layer formed by the printing almost inevitably has a thickness of 0.3 µm to 30 µm, and thus it is not preferred. In the case of the printing, precise control of the film thickness is difficult, and thus there is a problem that a difference in blood sugar level of each measurement with a blood sugar level sensor becomes wider. A vacuum deposition method, such as a sputtering method, is more suitable in that a precise control of film thickness is possible, so that a measurement difference of a blood sugar level can be minimized.

CITATION LIST

Patent Document

PTD 1: Japanese Patent Laying-Open No. 2011-050300
PTD 2: National Patent Publication No. 2012-524903
PTD 3: Japanese Patent Laying-Open No. 2013-164350

SUMMARY OF INVENTION

Technical Problems

Accordingly, in view of the above existing problems, an object of the present invention is to provide a thin film-laminated film that has high chemical stability even at low costs and that can preferably be used as an electrode film of a strip for a blood sugar level sensor.

Solution to Problems

Accordingly, the present invention includes following constitutions.
1. A thin film-laminated film including a film substrate, and a titanium thin film and a carbon thin film laminated in this order on at least one surface of the film substrate.
2. The thin film-laminated film according to above 1, wherein the titanium thin film has a film thickness of from 10 to 400 nm, and the carbon thin film has a film thickness of from 0.2 to 50 nm.
3. The thin film-laminated film according to the above 1 or 2, wherein the thin film-laminated film shows a peak oxidation current at a potential between +0.2 V and +0.6 V, and a peak reduction current at a potential between 0 V and +0.4 V in a cyclic voltammetry measurement of ferrocyanide ions using silver/silver chloride as a reference electrode.
4. The thin film-laminated film according to the above 1 to 3, wherein the film substrate has a total light transmittance of less than or equal to 50%.
5. The thin film-laminated film according to the above 1 to 4, wherein the film substrate has a reflectance of greater than or equal to 50%.
6. A strip for a blood sugar level sensor, including the thin film-laminated film according to any of the above 1 to 5.
7. A blood sugar level sensor device including the strip for a blood sugar level sensor according to above 6.

Advantageous Effects of Invention

According to the present invention, it has been made possible to provide a thin film-laminated film that has high chemical stability even at low costs and that can preferably be used as an electrode film of a strip for a blood sugar level sensor. Further, a stable electrical signal can be obtained from a blood sugar level sensor with a strip for a blood sugar level sensor in which the thin film-laminated film according to the present invention is used as an electrode.

DESCRIPTION OF EMBODIMENTS

A thin film-laminated film according to the present invention is a film, in which a titanium thin film is laminated on at least one surface of a film substrate directly or with other layer imposed therebetween, and then a carbon thin film is further laminated on the titanium thin film.

It has been found out that a titanium thin film is chemically stable, so that the titanium thin film is not dissolved from a surface by contact with a reagent layer, and is not dissolved from a lateral face by contact with a reagent layer even when being subjected to pattern processing. In addition, the titanium thin film has an advantage of low electrical resistance, and thus is superior in electrical conductivity. Accordingly, it has been considered that the titanium thin film can preferably be used as an electrode film of a strip for a blood sugar level sensor. On the other hand, however, it is apparent that the titanium thin film does not have characteristics to donate and accept electrons to/from an electron mediator. Thus, when the titanium thin film is used solely, it is not possible to use the titanium thin film preferably as an electrode film for a blood sugar level sensor.

On the other hand, a carbon thin film is chemically stable, and thus the carbon thin film is not dissolved by contact with a reagent layer. In addition, in a form of a bulk material, donation and acceptance of electrons to/from an electron mediator can be performed, and thus is a possible material to be used solely as an electrode film for a blood sugar level sensor. However, in a form of an ultra thin film, the carbon thin film has high electrical resistance, so that it is difficult to donate and accept electrons. The present invention has a constitution to actively make use of the advantage of the carbon thin film to donate and accept electrons to/from an electron mediator, and then to compensate the poor electrical conductivity of the carbon thin film with the superior electrical conductivity of the titanium thin film. In the present invention, it is firstly discovered that an ultra thin carbon film having no ability to donate and accept electrons can acquire the ability by lamination with a titanium thin film. On the other hand, in the above-cited literature 2, it is not suggested that the carbon layer donates and accepts electrons to/from an electron mediator. The literature discloses an idea that the nickel layer solely exerts the function to donate and accept electrons, and the carbon layer covers the nickel layer to protect the nickel layer from its weakness against an acid and an alkali. Accordingly, the cited literature 2 has a technical idea completely different from that of the present invention. The titanium thin film according to the present invention is in itself resistant to an acid and an alkali, and thus is not particularly required to be protected in use for an electrode film for a blood sugar level sensor. Even when the carbon thin film is excessively thin, for example less than or equal to 20 nm, and thus an electron mediator in a reagent layer passes through the carbon layer, the titanium thin film is not dissolved. In the present invention, the reason why the carbon thin film is laminated on the titanium thin film is not for the purpose of protecting the titanium thin film. Also in this point, the present invention has a technical idea completely different from that of the strip according to the above-cited literature 2, in which the carbon layer solely compensates for the weakness of the nickel layer against an acid and an alkali.

The titanium thin film preferably has a film thickness in the range of from 10 to 400 nm, more preferably from 15 to 250 nm, particularly preferably from 20 to 200 nm. When the film thickness of the titanium thin film is greater than or equal to 10 nm, a surface resistance value is reduced, and an electrical signal can surely be obtained when the thin film-laminated film is used as an electrode of a blood sugar level sensor, and thus it is preferred. On the other hand, when the film thickness is less than or equal to 400 nm, rigidity of the titanium thin film is not excessively high, and there is no risk of exfoliation and deterioration in adhesiveness, and a problem of warping of the substrate does not come up, and thus it is preferred. For example, when deposition is performed by a sputtering method, the film thickness can be controlled by changing a velocity of the film as passing over a titanium target, or by changing input electricity.

The carbon thin film preferably has a film thickness in the range of from 0.2 to 50 nm, more preferably from 0.25 to 30 nm, particularly preferably from 0.3 to 20 nm. When the film thickness is greater than or equal to 0.2 nm, it is possible to donate and accept electrons to/from an electron mediator, and an electrical signal can surely be obtained when the thin film-laminated film is used as an electrode of a strip for a blood sugar level sensor, and thus it is preferred. On the other hand, when the film thickness is less than or equal to 50 nm, adhesiveness to the titanium thin film is maintained, and it is not exfoliated from the titanium thin film, and there is no risk of cracking the titanium thin film, and thus it is preferred. When the carbon thin film is exfoliated from the titanium thin film, or the titanium thin film is cracked, it is difficult to operate the thin film-laminated film as an electrode of a strip for a blood sugar level sensor, and thus it is not much preferred. A film thickness of less than or equal to 50 nm is a practicable film thickness in an industrial vacuum deposition method, and thus it is preferred. For example, when deposition is performed by a sputtering method, the film thickness can be controlled by changing a velocity of the film as passing over a carbon target, or by changing input electricity.

In the present invention, the thin film-laminated film preferably shows a peak oxidation current at a potential between +0.2 V and +0.6 V in a cyclic voltammetry measurement of ferrocyanide ions using silver/silver chloride as a reference electrode. It means that even when a positive voltage is applied, the laminated thin film of titanium and carbon according to the present invention is not dissolved with ionization, and can oxidize ferrocyanide ions to ferricyanide ions, that is to say, can donate and accept electrons to/from an electron mediator. A peak oxidation current observed outside of the above range is caused by oxidation of materials except for ferrocyanide ions, and thus it has no relation with proper operation as a blood sugar level sensor electrode. In addition, it can result in requirement of high voltage when the thin film-laminated film is operated as a blood sugar level sensor electrode, and thus it is not much preferred.

In the present invention, the thin film-laminated film preferably shows a peak reduction current at a potential between 0 V and +0.4 V. It means that the laminated thin film of titanium and carbon according to the present invention is not dissolved with ferricyanide ions, and can reduce ferricyanide ions to ferrocyanide ions, and that the thin film is not deteriorated even by the above positive voltage application. When the thin film is deteriorated, it does not show a reduction peak in the above range, and thus it is not preferred. Further, a peak reduction current observed outside of the above range is caused by reduction of materials except for a ferricyanide, and thus it has no relation with proper operation as a blood sugar level sensor electrode.

Absolute values of the peak oxidation current and the peak reduction current are greater than or equal to 0.05 mA and less than or equal to 2 mA under the conditions of Examples according to the present invention, whereas the values vary depending on measurement conditions. If the value is less than 0.05 mA, it is thought that there is no oxidation-reduction reaction of ferrocyanide ions and ferricyanide ions, and thus it is not much preferred. If the value is greater than 2 mA, there is a risk of elution of an electrode component, and thus it is not much preferred.

Ferrocyanide ions have the highest oxidation potential in electron mediators used in a blood sugar level sensor. As long as ferrocyanide ions can be oxidized, other mediators, such as ruthenium ions, are also appropriate.

The thin film-laminated film according to the present invention is preferably produced by laminating a titanium thin film on at least one surface of the film substrate directly or with other layer interposed therebetween by vacuum deposition, and then laminating a carbon thin film on the titanium thin film by vacuum deposition without contact with the air as much as possible. The titanium thin film is contaminated/oxidized by contact with the air, and thus an adhesion force between the titanium thin film and the carbon thin film is decreased. This result in exfoliation of the carbon thin film from the titanium thin film during the cyclic voltammetry measurement, and thus it may be difficult to obtain an appropriate result. In a film roll, as long as it is not unwound in the air after lamination of the titanium thin film, it can be stored for up to 24 hours in the air. The film roll is not easily in contact with the air, so that it can be stored for some period in the air. However, when it is unwound, it can be stored for up to 1 hour or so in the air.

In the thin film-laminated film according to the present invention, a substrate film having a total light transmittance of less than or equal to 50% can preferably be used. The reason is that when this kind of film substrate is used, pattern processability with a laser can be improved.

The thin film-laminated film according to the present invention will be described with respect to each layer in detail.

(Film Substrate)

The film substrate used in the present invention is a film, in which an organic polymer is melt extruded or solution extruded to form a film-like form, and the resulting form is optionally subjected to treatments of stretching in a longitudinal direction and/or width direction, heat fixation, heat relaxation, and the like. Examples of the organic polymers include polyethylene, polypropylene, polyethylene terephthalate, polyethylene-2,6-naphthalate, polypropylene terephthalate, polybutylene terephthalate, nylon 6, nylon 4, nylon 66, nylon 12, polyimide, polyamide imide, polyethersulfane, polyether ether ketone, polycarbonate, polyarylate, cellulose propionate, polyvinyl chloride, polyvinylidene chloride, polyvinyl alcohol, polyether imide, polyphenylene sulfide, polyphenylene oxide, polystyrene, syndiotactic polystyrene, and norbornene-based polymer.

Among the organic polymers, polyethylene terephthalate, polypropylene terephthalate, polybutylene terephthalate, polyethylene-2,6-naphthalate, syndiotactic polystyrene, norbornene-based polymer, polycarbonate, polyarylate, and the like are preferred. In addition, a monomer of other organic polymer in a small amount may be copolymerized with the organic polymers, and other organic polymers may be blended.

A thickness of the film substrate used in the present invention is preferably from 10 to 300 μm, more preferably from 20 to 250 μm. If the thickness of a plastic film is less than 10 μm, mechanical strength tends to be insufficient, it is difficult to handle a sensor, such as a blood sugar level sensor, and thus it is not preferred. On the other hand, if the thickness is greater than 300 μm, a thickness of a sensor, such as a blood sugar level sensor, becomes excessively thick, and thus it is not preferred.

When an electrode film for a blood sugar level sensor and the like is manufactured, the thin film is subjected to patterning. The thin film is subjected to laser processing as one of patterning methods (e.g., see Japanese Patent Laying-Open No. H09-189675). In the laser processing, it is preferable that the thin film can be removed from the electrode film by low laser power in view of production. In the present invention, in order to improve pattern processability with a laser, a film having a total light transmittance of less than or equal to 50% and/or a reflectance of greater than or equal to 50% can be used. As this kind of the film substrate, a white film can preferably be used. It has been found out that operation efficiency of the pattern processing with a laser is improved by using the film having a total light transmittance of less than or equal to 50% and/or a reflectance of greater than or equal to 50% as the film substrate as compared to the case of using a colorless and transparent film substrate, when patterning is performed by partially removing the thin film (when an intermediate layer is exist, the intermediate layer may be concurrently removed) with a laser.

As the film substrate having a total light transmittance of less than or equal to 50% and/or a reflectance of greater than or equal to 50%, a void-containing film substrate having a void content of from 3 to 50 vol % can preferably be used. When the void content is greater than or equal to 3%, it is easy to achieve a total light transmittance of less than or equal to 50% and/or a reflectance of greater than or equal to 50%, and thus it is preferred. On the other hand, when the void content is less than or equal to 50%, sufficient strength as a substrate can be achieved, and thus it is preferred. In order to introduce voids, a method including admixing an organic polymer (a thermoplastic resin) constituting the substrate film with an immiscible thermoplastic resin, melt extruding the mixture, cooling and solidifying the mixture, and then stretching the mixture in at least one axial direction to introduce voids can preferably be employed. When the organic polymer constituting the substrate film is polyester, thermoplastic resins immiscible with the above polyester include polyolefins including polyethylene, polypropylene, polymethyl pentene, and the like as typical examples, polystyrene, cyclic polyolefin, polyacrylic resin, polycarbonate, polysulfone, a cellulose-based resin, and the like.

In addition, as the film substrate having a total light transmittance of less than or equal to 50% and/or a reflectance of greater than or equal to 50%, a film substrate containing a white filler, such as titanium oxide, barium sulfate, calcium carbonate, silica, aluminum oxide, organic particles, and the like can preferably be used. Especially, a film substrate containing titanium oxide or barium sulfate having a high refractive index can preferably be used. A content of the white filler is preferably in the range of from 0.2 to 50 wt %. When the content of the white filler is greater than or equal to 0.2 wt %, the total light transmittance can easily be reduced, and the reflectance can easily be increased, and thus it is preferred. On the other hand, when the content of the white filler is less than or equal to 50 wt %, sufficient strength as a substrate can be maintained, and thus it is preferred.

In the present invention, as the substrate film, a laminated body of a void-containing layer and a white filler-containing layer can preferably be used as long as the laminated body has a total light transmittance of less than or equal to 50% and/or a reflectance of greater than or equal to 50%. In this case, the void-containing layer may be placed outside or may be placed inside.

In addition, a single layer may contain both voids and a white filler. Furthermore, a void-containing layer and a void-free layer can be laminated. When the void-containing layer is expressed as Layer A and the void-free layer is expressed as Layer B, laminated structures of Layer A/Layer B, Layer B/Layer A/Layer B, and Layer B/Layer A/other Layer C can be employed. A film substrate having these laminated structures having a total light transmittance of less than or equal to 50% is preferred in that surfaces of Layer B and Layer C are smooth. A layer thickness ratio of Layer A:Layer B of greater than or equal to 2:1 is effective to reduce the total light transmittance owing to inclusion of voids, and a ratio of greater than or equal to 4:1 is more preferred. However, when a layer thickness ratio of Layer B is excessively small, film formation may be difficult, and thus a layer thickness ratio of Layer A:Layer B is preferably less than or equal to 20:1. When a constitution contains a plurality of Layers B in the film substrate, a total thickness of Layers B is used for the calculation.

In the film substrate used in the present invention, a film as described above can be subjected to a surface activation treatment, such as a corona discharge treatment, a glow discharge treatment, a flame treatment, an ultraviolet ray irradiation treatment, an electron beam irradiation treatment, or an ozone treatment, as long as the object of the present invention is not impaired. In addition, an anchor coating layer can be formed on the film substrate for the purpose of giving an easy-adhesive property, and the like.

In the film substrate used in the present invention, a cured material layer containing a curing-type resin as a main constituent is also preferably formed for the purpose of improving adhesiveness to the titanium thin film, giving a chemical resistance property, and preventing precipitation of a low molecular weight substance such as an oligomer.

The above curing-type resin is not particularly limited as long as it is a resin cured by energy application such as heating, ultraviolet ray irradiation, or electron beam irradiation, and includes a silicone resin, an acrylic resin, a methacrylate resin, an epoxy resin, a melamine resin, a polyester resin, and an urethane resin.

(Titanium Thin Film)

The titanium thin film preferably has a film thickness in the range of from 10 to 400 nm, more preferably from 15 to 250 nm, particularly preferably from 20 to 200 nm. When the film thickness is greater than or equal to 10 nm, a surface resistance value is reduced, and an electrical signal can surely be obtained when the thin film-laminated film is used as an electrode of a blood sugar level sensor, and thus it is preferred. On the other hand, when the film thickness is less than or equal to 400 nm, rigidity of the titanium thin film is not excessively high, and there is no risk of exfoliation and deterioration in adhesiveness, and a problem of warping of the substrate does not come up, and thus it is preferred. For example, when deposition is performed by a sputtering method, the film thickness can be controlled by changing a velocity of the film as passing over a titanium target, or by changing input electricity. The titanium thin film in itself cannot donate and accept electrons to/from an electron mediator. However, a carbon thin film that can donate and accept electrons to/from an electron mediator is laminated on the titanium thin film, and thus the laminated film is preferable as an electrode film for a blood sugar level sensor.

The titanium thin film can contain carbon for the purpose of improving an adhesion force to the carbon thin film. A content of carbon is preferably less than or equal to 50 at % to maintain electrical conductivity. A composite layer composed of titanium and carbon can be formed between the titanium thin film and the carbon thin film. In this case, the composite layer can have a film thickness of from 0.2 to 20 nm, and a proportion of carbon in the composite layer can be from 3 at % to 97 at %.

(Carbon Thin Film)

The carbon thin film preferably has a film thickness in the range of from 0.2 to 50 nm, more preferably from 0.25 to 30 nm, particularly preferably from 0.3 to 20 nm. When the film thickness is greater than or equal to 0.2 nm, it is possible to donate and accept electrons to/from an electron mediator, and an electrical signal can surely be obtained when the thin film-laminated film is used as an electrode of a strip for a blood sugar level sensor, and thus it is preferred. On the other hand, when the film thickness is less than or equal to 50 nm, exfoliation caused by deterioration of adhesiveness to the titanium thin film does not occur, and there is no risk of cracking the titanium thin film, and thus it is preferred. When the carbon thin film is exfoliated from the titanium thin film, or the titanium thin film is cracked, it becomes difficult to operate the thin film-laminated film as an electrode of a strip for a blood sugar level sensor, and thus it is not preferred. A film thickness of less than or equal to 50 nm is a practicable film thickness in an industrial vacuum deposition, and thus it is preferred. For example, when deposition is performed by a sputtering method, the film thickness can be controlled by changing a velocity of the film as passing over a carbon target, or by changing input electricity. The carbon thin film may contain titanium as described below. However, the carbon thin film preferably contains no organic matter, such as a binder resin. In addition, the carbon thin film is an extremely thin film of from 0.2 to 50 nm, and has some difficulty in electrical conductivity. However, due to electrical conductivity of the titanium thin film placed between the film substrate and the carbon thin film, the thin film-laminated film is preferable as an electrode film for a blood sugar level sensor.

In the present invention, carbon is a material showing electron conductivity due to existence of a double bond between carbon atoms. Graphite, amorphous carbon, graphene, diamond-like carbon, and the like are within the above definition. Especially, isotropic graphite can preferably be used since it can be produced at the lowest cost. Diamond is not included which does not have a double bond between carbon atoms and does not have electron conductivity.

The carbon thin film can contain titanium for the purpose of improving an adhesion force to the titanium thin film. A content of titanium is preferably less than or equal to 50 atom % to maintain the characteristics to donate and accept electrons to/from an electron mediator.

(Deposition Method)

As deposition methods of the thin film according to the present invention, a vacuum vapor-deposition method, a sputtering method, a CVD method, an ion plating method, a spray method, and the like are known. The method described above can appropriately be used depending on a required film thickness. However, a sputtering method and an evaporation method are preferred, and a sputtering is particularly preferred since high sticking power is exerted, a variation in film thickness is reduced, and a change in a blood sugar level when used as a blood sugar level sensor is diminished.

In this case, a means such as plasma irradiation, ion assist, or the like may be used in combination with the above method. A bias, such as a direct current, an alternating current, or high frequency waves, maybe applied to a substrate board, as long as the object of the present invention is not impaired.

For example, when the deposition is performed by a sputtering method, it is preferred that prior to sputtering, a vacuum chamber is evacuated to a degree of vacuum of a pressure less than or equal to 0.0005 Pa (ultimate vacuum is less than or equal to 0.0005 Pa), and then an inert gas, such as Ar, is introduced into the vacuum chamber, and an electric discharge is generated under the pressure range of from 0.01 to 10 Pa to perform sputtering. Especially, in view of productivity, a DC sputtering method is preferred, and a DC magnetron sputtering method is more preferred. In addition, the same is true in other methods such as a vapor-deposition method and a CVD method.

It is preferred that after the titanium thin film is laminated, the carbon thin film is laminated without contact with the air as much as possible. A surface of the titanium thin film is contaminated/oxidized by contact with the air, and thus an adhesion force between the titanium thin film and the carbon thin film is decreased. If the carbon thin film is exfoliated from the titanium thin film during a cyclic voltammetry measurement, an appropriate result becomes difficult to obtain, and thus it is not preferred. In a film roll, as long as it is not unwound in the air after lamination of titanium, it can be stored for up to 24 hours in the air. The film roll is not easily in contact with the air, so that it can be stored for some period in the air. When it is unwound, it can be stored for up to 1 hour or so in the air.

An especially preferable embodiment is to employ a production method including laminating a titanium thin film on at least one surface of a film substrate by a vacuum deposition method, and then laminating a carbon thin film by a vacuum deposition method substantially without contact with the air. The term "substantially without contact with the air" refers to employing a production process having no contact with the air after deposition of the titanium thin film until deposition of the carbon thin film in such a manner that in a vacuum chamber of a sputtering production apparatus, the titanium thin film is sputtered, and then the carbon thin film is continuously sputtered while keeping the vacuum state.

Figure 1:
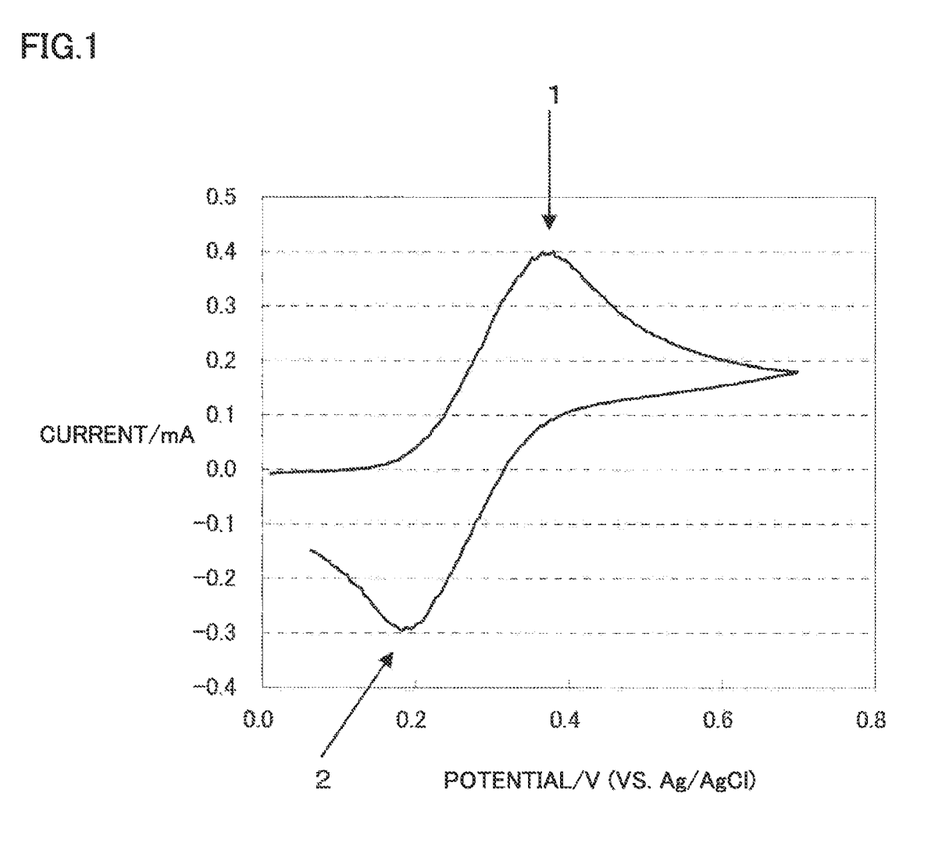
FIG. 1 is a cyclic voltammogram of a cyclic voltammetry measurement result for a thin film-laminated film of Example 1.
Figure 2:
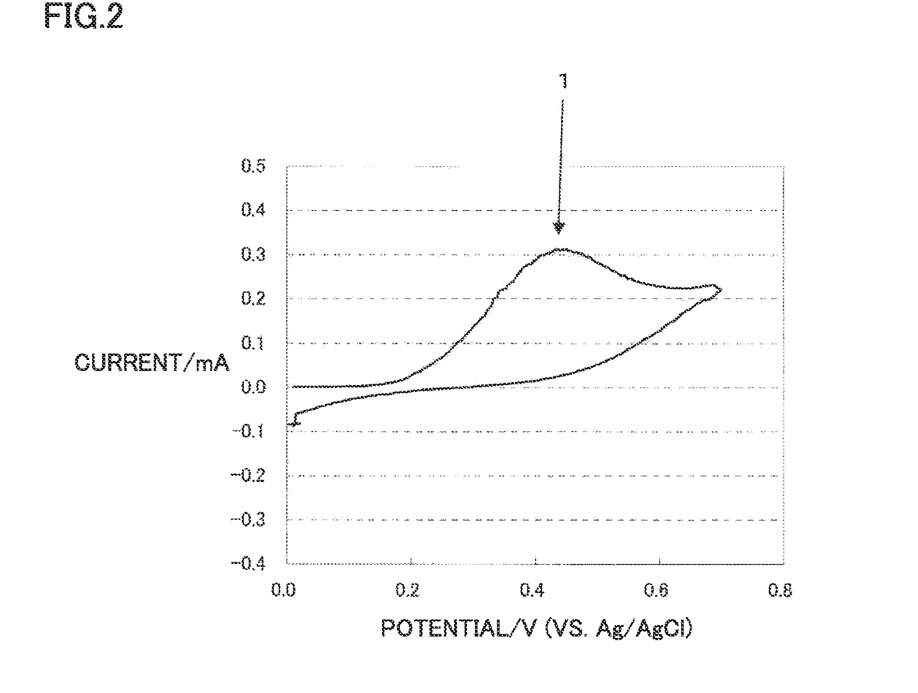
FIG. 2 is an example unfavorable in that a peak reduction current is not observed in a cyclic voltammogram of a cyclic voltammetry measurement result for a thin film-laminated film.

In each of Examples as described below, a titanium thin film is laminated on a film substrate in a vacuum chamber, and continuously, without contact with the air, a carbon thin film is laminated on the titanium thin film in the same vacuum chamber, and thus a required adhesion force is retained between the titanium thin film and the carbon thin film. In a cyclic voltammetry measurement, an appropriate result showing a peak oxidation current at a potential between +0.2 V and +0.6 V, and a peak reduction current at a potential between 0 V and +0.4 V is obtained (e.g., see FIG. 1 showing a cyclic voltammogram in Example 1). On the other hand, when a titanium thin film is laminated, and after storing in the air for, for example, 48 hours or so, a carbon thin film is laminated on the titanium thin film, an adhesion force between the titanium thin film and the carbon thin film is decreased. Thus, when a cyclic voltammetry (CV) measurement is performed, a preferable result showing a peak oxidation current at a potential between +0.2 V and +0.6 V, and a peak reduction current at a potential between 0 V and +0.4 V may not always be obtained. For example, FIG. 2 shows an example that is not much preferable in that when a titanium thin film is laminated, and after storing in the air for 48 hours or so, a carbon thin film is laminated on the titanium thin film to provide a thin film-laminated film, the carbon thin film is exfoliated during the measurement, and although a peak oxidation current is observed, a peak reduction current is not observed.

The thin film-laminated film according to the present invention obtained as described above is subjected to patterning such as laser processing, and then it is preferably used as an electrode film of a strip for a blood sugar level sensor. The thin film-laminated film is formed into a strip for a blood sugar level sensor according to types of blood sugar level sensor devices, and the strip is installed in a device for a blood sugar level sensor, and used.

EXAMPLES

Hereinafter, the present invention will be described much more in detail with reference to Examples, but the present invention is not limited by Examples in any way. Each of properties of a thin film-laminated film is measured by a method described below.

(1) Film Thickness of Thin Film

A micro thin section (5 μm in width, 100 nm in depth) was prepared by focused ion beam, and then the micro thin section was photographed using a transmission electron microscope (JEM-2010, manufactured by JEOL LTD.), at an acceleration voltage of 200 kV, by bright field observation, and with an observation magnification of 200,000×. Then, a film thickness was determined from the obtained photograph.

(2) Cyclic Voltammetry Measurement

A thin film-laminated film was cut into strip-like shape (50 mm×5 mm in width). In an aqueous solution containing 5 mM potassium ferrocyanide and 1 M potassium nitrate was immersed 10 mm of the strip-like shaped thin film-laminated film. Silver/silver chloride as a reference pole and a platinum coil as a counter pole were also placed in the solution. Voltages versus silver/silver chloride were set as follows: initial voltage=+0 V, switching voltage=+0.7 V, and final voltage=0 V. Then, a measurement was performed at a scan rate of 50 mV/s. When a peak oxidation current was observed at a potential between +0.2 V and +0.6 V, and a peak reduction current was observed at a potential between 0 V and +0.4 V, the result was represented by "Observed" in Table 1. On the other hand, a peak oxidation current and/or a peak reduction current was not observed at the above potential, the result was represented by "Not observed" in Table 1.

(3) Change in Resistance Value after Application of Reagent Layer

A thin film-laminated film was cut into a square (50 mm×50 mm), and then a surface resistance was measured by a four-terminal method according to JIS-K7194. A measuring machine used was Lotest AMCP-T400 manufactured by Mitsubishi Petrochemical Co., Ltd.

An aqueous solution containing 5 wt % of polyvinyl pyrrolidone, 20 wt % of potassium ferricyanide, and 10 wt % of morphornoethanesulfonic acid was applied, and dried at 40° C. for 30 minutes. Then, the film was placed under a condition of 40° C., 90% RH for 16 hours, and the chemical were washed off with water, and then a surface resistance value was measured. A surface resistance before the test was expressed as R0, and a surface resistance after the test was expressed as R1. When the values satisfied 0.95≤R1/R0≤1.05, the result was represented by "Within range", and when the ratio was outside of the range, the result was represented by "Out of range".

(4) Dissolution of Slit Portion after Application of Reagent Layer

As a model test for identifying whether a problem that a metal thin film is eluted when the metal thin film is in contact with a reagent layer at a lateral face of a patterned electrode, the following evaluation was performed.

A thin film-laminated film was slit (20 mm in length), but the substrate film was not cut off. An aqueous solution containing 5 wt % of polyvinyl pyrrolidone, 20 wt % of potassium ferricyanide, and 10 wt % of morphornoethanesulfonic acid was applied, and dried at 40° C. for 30 minutes. Then, the film was placed under a condition of 40° C., 90% RH for 16 hours, and the chemical were washed off with water. An area around the slit portion was magnified by a loupe and observed. When dissolution of the thin film was not occurred, the result was represented by "Not occurred", and when dissolution was occurred, the result was represented by "Occurred".

(5) Nd:YAG Laser Processing in Examples 7 to 12

A continuous-wave Nd:YAG laser (YLR-200-AC) manufactured by IPG Photonics Corporation was used. An irradiation spot diameter was set to 30 μm, and an irradiation frequency was set to 1 irradiation/1 dot. Then, a laser was irradiated with varying laser power to enable removal of a thin film (when a carbon thin film, a titanium thin film, and an intermediate layer were present, the intermediate layer was also to be removed) in a line (0.5 mm in width, 20 mm in length). A rectangular strip (10 mm in width) was cut out in perpendicular orientation to the irradiated line, and then electrical resistance between two points, that is, across the irradiated portion, was measured. In each Example, a minimum laser power where a measurement of resistance value became impossible was referred to as P1 (W). In addition, a thin film having the same constitution as that of a thin film according to each Example was laminated on a biaxially-oriented polyester film substrate having a total light transmittance of 88%, and a reflectance of 4.5%. Then, in the same manner as above, a minimum laser power where a measurement of a resistance value became impossible was referred to as P2 (W). When the values satisfy P1/P2≤0.95, the result shows that laser processability was improved.

(6) $CO_2$ Laser Processing in Examples 7 to 12

A $CO_2$ laser (VersaLaser) manufactured by Laser Works Inc. was used. A spot diameter was set to 72 μm, and an irradiation rate was set to 1270 mm/second. Then, a laser was irradiated with varying laser power to enable removal of an inorganic thin film (when a carbon thin film, a titanium thin film, and an intermediate layer were present, the intermediate layer was also to be removed) in a line (0.5 mm in width, 20 mm in length). A rectangular strip (10 mm in width) was cut out in perpendicular orientation to the irradiated line, and then electrical resistance between two points, that is, across the irradiated portion, was measured. In each Example, a minimum laser power where a measurement of a resistance value became impossible was referred to as P3 (W). In addition, a thin film having the same constitution as that of a thin film according to each Example was laminated on a biaxially-oriented polyester film substrate having a total light transmittance of 88%, and a reflectance of 4.5%. Then, in the same manner as above, a minimum laser power where a measurement of a resistance value became impossible was referred to as P4 (W). When the values satisfy P3/P4 0.95, the result shows that laser processability was improved.

(7) Total Light Transmittance of Film Substrate

A total light transmittance of a film substrate was measured with NDH-1001DP manufactured by NIPPON DENSHOKU INDUSTRIES CO., LTD. according to JIS-K7136. A surface to be measured is a film substrate surface on which a titanium thin film, a carbon thin film, and the like are laminated, or have been laminated.

When a transmittance of a substrate film is measured using a thin film-laminated film, a carbon thin film is removed by plasma etching, and a titanium thin film is dissolved by 30 mass % of hydrochloric acid, and then a measurement is performed (When the film substrate has a cured material layer on its surface, the substrate film and the cured material layer are considered as a single body of a film substrate, and a total light transmittance is measured without removing the cured material layer.).

(8) Reflectance of Film Substrate

A spectrophotometer (UV-vis UV-3150) manufactured by SHIMADZU CORPORATION was equipped with an integrating sphere, and a reflectance was measured over 400 to 700 nm (reflectance of a standard white board of barium sulfate was considered as 100%). On this occasion, a surface to be measured is a film substrate surface on which a titanium thin film, a carbon thin film, and the like are laminated, or have been laminated. Then, a black sheet (GA BOARD-FS BLACK 26) is put on an opposite side, and a measurement is performed. A reflectance was read from the obtained chart at intervals of 5 nm, and then its arithmetic mean value was regarded as a reflectance.

When a reflectance of a substrate film is measured using a thin film-laminated film, a carbon thin film is removed by plasma etching, and a titanium thin film is dissolved by 30 mass % of hydrochloric acid, and then a measurement was performed (When the film substrate has a cured material layer on its surface, the substrate film and the cured material layer are considered as a single body of a film substrate, and a reflectance is measured without removing the cured material layer.).

(9) Void Content of Film Substrate

A cross-section of a film was photographed using a scanning electron microscope (SU1510 manufactured by Hitachi High-Technologies Corporation), and voids of each region were picked using a general purpose image analysis software (ImageJ). Then, a void content was determined as an area ratio, and the value was presented as vol % as it was.

Example 1

As a plastic film, a biaxially-oriented polyethylene terephthalate-based film having a thickness of 250 μm (E5001, manufactured by TOYOBO CO., LTD.) was used. The plastic film had a total light transmittance of 88%, and a reflectance of 4.5%.

A roll of the biaxially-oriented polyethylene terephthalate-based film was exposed to vacuum. In a vacuum chamber, a rewind treatment was performed under a pressure of $2 \times 10^{-3}$ Pa, and an exposure time of 20 minutes. In addition, a setting temperature of a center roll was 40° C.

Then, a titanium thin film was deposited on one side of the biaxially-oriented polyester film by using a titanium target. On this occasion, an ultimate pressure in the vacuum chamber before sputtering was confirmed to be $1 \times 10^{-4}$ Pa (ultimate vacuum), and then sputtering was performed. A condition of the sputtering was application of DC electricity of 3 W/square. A deposition was performed by a DC magnetron sputtering method under a 0.4 Pa atmosphere with Ar gas flow. In addition, a center roll setting temperature was 0° C. As described above, a titanium thin film having a film thickness of 50 nm was deposited.

Next, without contact with the air, a carbon thin film was sputtered in the same vacuum chamber in the same manner to laminate the carbon thin film on the titanium thin film. A film thickness of the carbon thin film was set to 2 nm.

FIG. 1 is a measurement result of a cyclic voltammetry (CV). A peak oxidation current was observed as an electric current value of +0.39 mA at a potential of +0.38 V, and a peak reduction current was observed as an electric current of −0.3 mA at a potential of +0.18 V. Thus, the titanium-carbon thin film-laminated film can preferably be used as an electrode of a strip for a blood sugar level sensor. In addition, there was no change in resistance value, and no dissolution from the slit portion after application of the reagent layer. Thus, the titanium-carbon thin film-laminated film has high stability, and can preferably be used as an electrode of a strip for a blood sugar level sensor.

Example 2

Example 2 was carried out in the same manner as in Example 1 except that a titanium thin film having a film thickness of 100 nm was laminated, and a carbon thin film having a film thickness of 0.25 nm was further laminated on the titanium thin film. A peak oxidation current and a peak reduction current were observed at preferable potentials. Thus, the resulting product can preferably be used as an electrode of a strip for a blood sugar level sensor. In addition, there was no change in resistance value, and no dissolution from the slit portion after application of the reagent layer. Thus, the titanium-carbon thin film-laminated film has high stability, and can preferably be used as an electrode of a strip for a blood sugar level sensor.

Example 3

Example 3 was carried out in the same manner as in Example 1 except that a titanium thin film having a film thickness of 25 nm was laminated, and a carbon thin film having a film thickness of 0.5 nm was further laminated on the titanium thin film. As shown in Table 1, a peak oxidation current and a peak reduction current were observed at preferable potentials. Thus, the resulting product can preferably be used as an electrode of a strip for a blood sugar level sensor. In addition, there was no change in resistance value, and no dissolution from the slit portion after application of the reagent layer. Thus, the titanium-carbon thin film-laminated film has high stability, and can preferably be used as an electrode of a strip for a blood sugar level sensor.

Example 4

Example 4 was carried out in the same manner as in Example 1 except that a titanium thin film having a film thickness of 300 nm was laminated, and a carbon thin film having a film thickness of 5 nm was further laminated on the titanium thin film by vacuum vapor-deposition with electron beam heating. A peak oxidation current and a peak reduction current were observed at preferable potentials. Thus, the resulting product can preferably be used as an electrode of a strip for a blood sugar level sensor. In addition, there was no change in resistance value, and no dissolution from the slit portion after application of the reagent layer. Thus, the titanium-carbon thin film-laminated film has high stability, and can preferably be used as an electrode of a strip for a blood sugar level sensor.

Example 5

Example 5 was carried out in the same manner as in Example 1 except that a titanium thin film having a film thickness of 100 nm was laminated, and a carbon thin film having a film thickness of 40 nm was further laminated on the titanium thin film by vacuum vapor-deposition with electron beam heating. A peak oxidation current and a peak reduction current were observed at preferable potentials. Thus, the resulting product can preferably be used as an electrode of a strip for a blood sugar level sensor. In addition, there was no change in resistance value, and no dissolution from the slit portion after application of the reagent layer. Thus, the titanium-carbon thin film-laminated film has high stability, and can preferably be used as an electrode of a strip for a blood sugar level sensor.

Example 6

A mixed solvent of toluene/MEK (80/20: ratio by mass) as a solvent was added to 100 parts by mass of a photopolymerization initiator-containing ultraviolet ray curing-type acrylic resin (SEIKABEAM EXF-01J, manufactured by Dainichiseika Color & Chemicals Mfg. Co., Ltd.) so that a solid content concentration was 50 mass %, and then the resultant was stirred to dissolve homogeneously, so that an application liquid was prepared.

On an easy-adhesive layer of a biaxially-oriented polyethylene terephthalate-based film having an easy-adhesive layer on its surface (A4100, manufactured by TOYOBO CO., LTD.) (film thickness: 188 μm), the prepared application liquid was applied using a Meyer bar so that a coating film thickness was 3000 nm. After drying at 80° C. for 1 minute, ultraviolet rays were irradiated (exposure dose: 300 mJ/square) using an ultraviolet ray irradiation apparatus (model: UB042-5AM-W, manufactured by EYE GRAPHICS CO., LTD.) to cure the coating film, and then a cured material layer was laminated.

Example 6 was carried out in the same manner as in Example 1 except that a titanium thin film having a film thickness of 25 nm was laminated, and a carbon thin film having a film thickness of 20 nm was further laminated on the titanium thin film by vacuum vapor-deposition with electron beam heating. A peak oxidation current and a peak reduction current were observed at preferable potentials. Thus, the resulting product can preferably be used as an electrode of a strip for a blood sugar level sensor. In addition, there was no change in resistance value, and no dissolution from the slit portion after application of the reagent layer. Thus, the titanium-carbon thin film-laminated film has high stability, and can preferably be used as an electrode of a strip for a blood sugar level sensor.

Comparative Example 1

Figure 3:
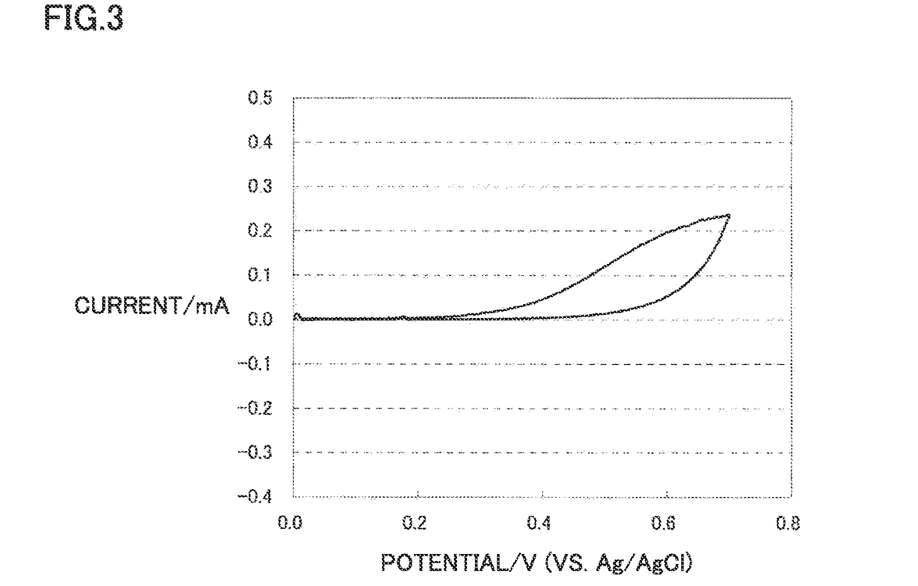
FIG. 3 is a cyclic voltammogram of a cyclic voltammetry measurement result for a thin film-laminated film of Comparative Example 1.

Comparative Example 1 was carried out in the same manner as in Example 1 except that only a titanium thin film having a film thickness of 100 nm was laminated by a sputtering method. As shown in FIG. 3, since a titanium thin film cannot donate and accept electrons to/from an electron mediator, a peak oxidation current and a peak reduction current are not observed at a potential. Thus, the resulting product is not much preferable for use as an electrode of a strip for a blood sugar level sensor.

Comparative Example 2

Figure 4:
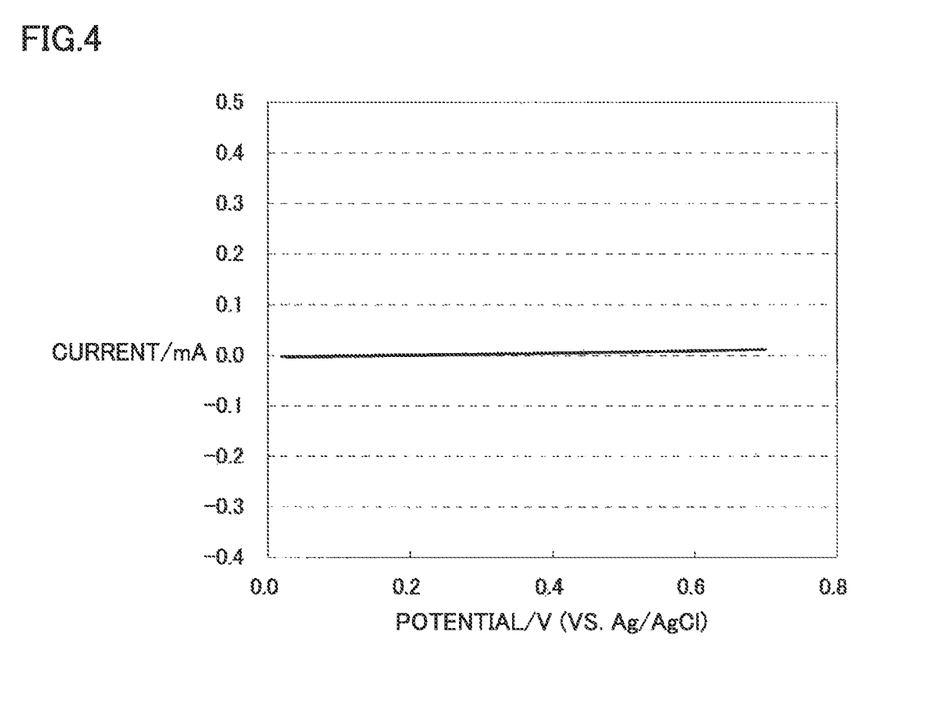
FIG. 4 is a cyclic voltammogram of a cyclic voltammetry measurement result for a thin film-laminated film of Comparative Example 2.

Comparative Example 2 was carried out in the same manner as in Example 1 except that only a carbon thin film having a film thickness of 40 nm was laminated by vacuum vapor-deposition with electron beam heating. As shown in FIG. 4, since the carbon thin film has a low electrical conductivity, a peak oxidation current and a peak reduction current are not observed at a potential. Thus, the resulting product is not much preferable for use as an electrode of a strip for a blood sugar level sensor.

Comparative Example 3

Comparative Example 3 was carried out in the same manner as in Example 1 except that a titanium thin film having a film thickness of 100 nm was laminated, and a carbon thin film having a film thickness of 60 nm was further laminated on the titanium thin film by a vacuum vapor-deposition with electron beam heating. The carbon thin film and the titanium thin film were exfoliated, and thus it could not be referred to as a completed product of a thin film-laminated film. As a result, the titanium thin film is cracked, and thus a peak oxidation current and a peak reduction current are not observed at a potential. Thus, the resulting product is not much preferable for use as an electrode of a strip for a blood sugar level sensor.

Comparative Example 4

Comparative Example 4 was carried out in the same manner as in Example 1 except that a nickel thin film having a film thickness of 100 nm was laminated, and a carbon thin film having a film thickness of 2 nm was further laminated on the nickel thin film. There was a change in resistance value, and dissolution from the slit portion after application of the reagent layer. Thus, the resulting product is not much preferable for use as an electrode of a strip for a blood sugar level sensor.

Comparative Example 5

Comparative Example 5 was carried out in the same manner as in Example 1 except that a nickel thin film having a film thickness of 100 nm was laminated, and a carbon thin film having a film thickness of 40 nm was further laminated on the nickel thin film. Although there was no change in resistance value, but was dissolution from the slit portion after application of the reagent layer. Thus, the resulting product is not much preferable for use as an electrode of a strip for a blood sugar level sensor.

Comparative Example 6

Comparative Example 6 was carried out in the same manner as in Example 1 except that an aluminum thin film having a film thickness of 100 nm was laminated, and a carbon thin film having a film thickness of 40 nm was further laminated on the aluminum thin film. Although there was no change in resistance value, but was dissolution from the slit portion after application of the reagent layer. Thus, the resulting product is not much preferable for use as an electrode of a strip for a blood sugar level sensor. In addition, aluminum was dissolved from a lateral face during the cyclic voltammetry measurement, and thus the electrode was disappeared. For this reason, the resulting product is not much preferable for use as an electrode of a strip for a blood sugar level sensor.

Comparative Example 7

Comparative Example 7 was carried out in the same manner as in Example 1 except that a silver thin film having 100 nm was laminated, and a carbon thin film having a film thickness of 40 nm was further laminated on the silver thin film. Although there was no change in resistance value, but was dissolution from the slit portion after application of the reagent layer. Thus, the resulting product is not much preferable for use as an electrode of a strip for a blood sugar level sensor. In addition, silver was dissolved from a lateral face during the cyclic voltammetry measurement, and thus the electrode was disappeared. For this reason, the resulting product is not much preferable for use as an electrode of a strip for a blood sugar level sensor.

TABLE 1

|  | Titanium film thickness (nm) | Carbon film thickness (nm) | Intermediate layer between titanium and substrate | Cyclic voltammetry | Change in resistance value | Dissolution of slit portion |
| --- | --- | --- | --- | --- | --- | --- |
| Example 1 | 50 | 2 | — | Observed | Within range | Not occurred |
| Example 2 | 100 | 0.25 | — | Observed | Within range | Not occurred |
| Example 3 | 25 | 0.5 | — | Observed | Within range | Not occurred |
| Example 4 | 300 | 5 | — | Observed | Within range | Not occurred |
| Example 5 | 100 | 40 | — | Observed | Within range | Not occurred |
| Example 6 | 25 | 20 | Presence of cured material layer | Observed | Within range | Not occurred |
| Comparative Example 1 | 100 | — | — | Not observed | Within range | Not occurred |
| Comparative Example 2 | — | 40 | — | Not observed | Within range | Not occurred |
| Comparative Example 3 | 100 | 60 | — | Not observed | Within range | Not occurred |

TABLE 1-continued

|  | Titanium film thickness (nm) | Carbon film thickness (nm) | Intermediate layer between titanium and substrate | Cyclic voltammetry | Change in resistance value | Dissolution of slit portion |
|---|---|---|---|---|---|---|
| Comparative Example 4 | — (Nickel thin film thickness: 100 nm) | 2 | — | Observed | Out of range | Occurred |
| Comparative Example 5 | — (Nickel thin film thickness: 100 nm) | 40 | — | Observed | Within range | Occurred |
| Comparative Example 6 | — (Aluminum film thickness: 100 nm) | 40 | — | Not observed | Within range | Occurred |
| Comparative Example 7 | — (Silver film thickness: 100 nm) | 40 | — | Not observed | Within range | Occurred |

Example 7

A thin film was laminated in the same manner as in Example 1 with the use of, as a plastic film, a biaxially-oriented polyester film containing 10 wt % of rutile-type titanium oxide having an average particle size of 0.45 μm, as well as having a total light transmittance of 1.8%, a reflectance of 96.3%, and a thickness of 250 μm. As compared to the case of using a biaxially-oriented polyester film having a total light transmittance of 88% and a reflectance of 4.5% as a substrate (i.e., a film corresponding to Example 1), it was perceived that a laser power where a measurement of a resistance value became impossible was decreased, and thus the above case was far superior.

Example 8

A thin film was laminated in the same manner as in Example 2 with the use of a biaxially-oriented polyester film containing 20 wt % of barium sulfate having an average particle size of 0.3 μm, as well as having a total light transmittance of 1.9%, a reflectance of 96.1%, and a thickness of 250 μm. As compared to the case of using a biaxially-oriented polyester film having a total light transmittance of 88% and a reflectance of 4.5% as a substrate (i.e., a film corresponding to Example 2), it was perceived that a laser power where a measurement of a resistance value became impossible was decreased, and thus the above case was far superior.

Example 9

A thin film was laminated in the same manner as in Example 3 with the use of a biaxially-oriented polyester film containing 2 wt % of rutile-type titanium oxide having an average particle size of 0.45 μm, as well as having a total light transmittance of 44.4%, a reflectance of 51.3%, and a thickness of 250 μm. As compared to the case of using a biaxially-oriented polyester film having a total light transmittance of 88% and a reflectance of 4.5% as a substrate (i.e., a film corresponding to Example 3), it was perceived that a laser power where a measurement of a resistance value became impossible was decreased, and thus the above case was far superior.

Example 10

A thin film was laminated in the same manner as in Example 4 with the use of a biaxially-oriented polyester film containing 10 wt % of barium sulfate having an average particle size of 0.3 μm, as well as having a total light transmittance of 7.0%, a reflectance of 86.1%, and a thickness of 250 μm. As compared to the case of using a biaxially-oriented polyester film having a total light transmittance of 88% and a reflectance of 4.5% as a substrate (i.e., a film corresponding to Example 4), it was perceived that a laser power where a measurement of a resistance value became impossible was decreased, and thus the above case was far superior.

Example 11

A thin film was laminated in the same manner as in Example 5 with the use of a void-containing biaxially-oriented polyester film (the film was formed by mixing 80 wt % of polyethylene terephthalate and 20 wt % of polystyrene) having a thickness of 250 μm, a total light transmittance of 2.1%, and a reflectance of 95.7%. As compared to the case of using a biaxially-oriented polyester film having a total light transmittance of 88% and a reflectance of 4.5% as a substrate (i.e., a film corresponding to Example 5), it was perceived that a laser power where a measurement of a resistance value became impossible was decreased, and thus the above case was far superior.

Example 12

A cured material layer and a thin film were laminated in the same manner as in Example 6 with the use of a void-containing biaxially-oriented polyester film having a constitution of Layer B/Layer A/Layer B (layer thickness ratio: 1/8/1) and having a total light transmittance of 2.0%, a reflectance of 96.0%, and a total thickness of 250 μm, wherein Layer A was composed of 5 wt % of rutile-type titanium oxide having an average particle size of 0.45 μm and polyethylene terephthalate containing 15 wt % of polystyrene, and Layer B was composed of polyethylene terephthalate. As compared to the case of using a biaxially-oriented polyester film having a total light transmittance of 88% and a reflectance of 4.5% as a substrate (a film corresponding to Example 6), it was perceived that a laser power where a measurement of a resistance value became impossible was decreased, and thus the above case was far superior.

TABLE 2

| | Total light transmittance of substrate (%) | Reflectance of substrate (%) | Titanium film thickness (nm) | Carbon film thickness (nm) | Intermediate layer between titanium and substrate | Cyclic voltammetry | Change in resistance value | Dissolution of slit portion | Laser processability Nd:YAG P1/P2 | Laser processability $CO_2$ Laser P3/P4 |
|---|---|---|---|---|---|---|---|---|---|---|
| Example 7 | 1.8 | 96.3 | 50 | 2 | — | Observed | Within range | Not occurred | 0.67 | 0.80 |
| Example 8 | 1.9 | 96.1 | 100 | 0.25 | — | Observed | Within range | Not occurred | 0.71 | 0.82 |
| Example 9 | 44.4 | 51.3 | 25 | 0.5 | — | Observed | Within range | Not occurred | 0.80 | 0.89 |
| Example 10 | 7.0 | 89.6 | 300 | 5 | — | Observed | Within range | Not occurred | 0.75 | 0.83 |
| Example 11 | 2.1 | 95.7 | 100 | 40 | — | Observed | Within range | Not occurred | 0.71 | 0.82 |
| Example 12 | 2.0 | 96.0 | 25 | 20 | Presence of cured material layer | Observed | Within range | Not occurred | 0.60 | 0.78 |

INDUSTRIAL APPLICABILITY

A thin film-laminated film according to the present invention can preferably be used as an electrode film of a strip for a blood sugar level sensor, since the thin film-laminated film has high chemical stability and can donate and accept electrons to/from an electron mediator even at low costs. Thus, the present invention can contribute to provision of a high performance blood sugar level sensor device at low costs to society.

REFERENCE SIGNS LIST

1: Peak oxidation current
2: Peak reduction current

The invention claimed is:

1. A strip for a blood sugar level sensor, comprising a thin film-laminated film comprising a film substrate, and a titanium thin film and a carbon thin film laminated in this order on at least one surface of the film substrate,
wherein the titanium thin film has a film thickness of from 10 to 400 nm, the carbon thin film has a film thickness of from 0.2 to 50 nm,
wherein the carbon thin film consists of carbon,
wherein the titanium thin film substantially consists of titanium, and
wherein the film substrate consists of organic polymer.

2. The strip for a blood sugar level sensor according to claim 1, wherein the thin film-laminated film shows a peak oxidation current at a potential between +0.2 V and +0.6 V, and a peak reduction current at a potential between 0 V and +0.4 V in a cyclic voltammetry measurement of ferrocyanide ions using silver/silver chloride as a reference electrode.

3. The strip for a blood sugar level sensor according to claim 1, wherein the film substrate has a total light transmittance of less than or equal to 50%.

4. The strip for a blood sugar level sensor according to claim 1, wherein the film substrate has a reflectance of greater than or equal to 50%.

5. A blood sugar level sensor device comprising the strip for a blood sugar level sensor according to claim 1.

* * * * *